US007820437B2

(12) United States Patent
January et al.

(10) Patent No.: US 7,820,437 B2
(45) Date of Patent: Oct. 26, 2010

(54) CONSTITUTIVELY OPEN HERG (KV11.1) MUTANT CHANNELS

(75) Inventors: Craig T. January, Madison, WI (US); Christine Anne Klemens, Green Bay, WI (US); Brian Patrick Delisle, Lexington, KY (US); Blake D. Anson, Belleville, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 161 days.

(21) Appl. No.: 12/040,408

(22) Filed: Feb. 29, 2008

(65) Prior Publication Data

US 2009/0035804 A1    Feb. 5, 2009

Related U.S. Application Data

(60) Provisional application No. 60/892,691, filed on Mar. 2, 2007.

(51) Int. Cl.
*C12N 5/00*    (2006.01)
(52) U.S. Cl. .................................................. 435/325
(58) Field of Classification Search ........................ None
See application file for complete search history.

(56) References Cited

FOREIGN PATENT DOCUMENTS

WO    WO 01/58952 A    8/2001
WO    WO 2004/008103 A    1/2004

OTHER PUBLICATIONS

Christine A. Klemens, et al. "Intragenic Suppression of a Trafficking-Deficient hERG (Kv11.1) Mutation in the Voltage Sensor Yields a Constitutively Open Channel" (2007) Biophysical Journal, 121A.
Jun Chen, et al. "Position of Aromatic Residues in the S6 Domain, Not Inactivation, Dictates Cisapride Sensitivity of hERG and eag Potassium Channels" (2002) Proceedings of the National Academy of Sciences of the United States of America, 12461-12466.
Svetlana Z. Stepanovic, et al. "Gating and Drug Binding Properties of A653-hERG, a Highly Conserved Residue in K+ Channels" (2004) Biophysical Journal, 522a.
M. Zhang, et al. "Interactions Between Charged Residues in the Transmembrane Segments of the Voltage-Sensing Domain in the hERG Channel" (2005) Journal of Membrane Biology, 207(3):169-181.
JW Warmke, et al. "A Family of Potassium Channel Genes Related to eag in Drosophilia and Mammals" (1994) Proceedings of the National Academy of Science, 91(8):3438-3442.
PCT/US2008/055484 International Search Report dated Sep. 25, 2008.
Su Zhi, et al. "Mesoridazine: An open-channel blocker of human ether-a-go-go-related gene K+ channel" (2004) Journal of Molecular and Cellular Cardiology, 36(1):151-160.
Kamiya Kaichiro, et al. " Open Channel block of HERG K+ channels by vesnarinone" (2001) Molecular Pharmacology, 60(2):244-253.
Netzer Rainer, et al. "Screening lead compounds for QT interval prolongation" (2001) Drug Discovery Today, Elsevier, Rahway, NJ, US, 6(2):78-84.
PCT/US2008/055484 International Search Report dated Nov. 11, 2008.

*Primary Examiner*—Jon P Weber
*Assistant Examiner*—Bin Shen
(74) *Attorney, Agent, or Firm*—Quarles & Brady, LLP

(57)    ABSTRACT

We disclose a cell having double mutations of the hERG gene that lead to charge reversal amino acid substitutions at residues 466 and 534 of the wild type Kv11.1 channel protein. These double charge reversal mutations result in cells having constitutively open Kv11.1 channels. Such cells could be used in a method of testing development-stage drugs and other compounds for Kv11.1 channel block activity.

7 Claims, 4 Drawing Sheets

A.

B.

US 7,820,437 B2

CONSTITUTIVELY OPEN HERG (KV11.1) MUTANT CHANNELS

CROSS-REFERENCE TO RELATED APPLICATIONS

This application claims the benefit of U.S. Provisional Application No. 60/892,691, filed Mar. 2, 2007, which is incorporated by reference herein.

STATEMENT REGARDING FEDERALLY SPONSORED RESEARCH OR DEVELOPMENT

This invention was made with United States government support awarded by the following agencies: NIH NHLBI, Grant Number R01 HL60723. The United States government has certain rights in this invention.

BACKGROUND OF THE INVENTION

The present invention relates to cells having mutated hERG gene potassium channels (Kv11.1) that are constitutively open, specific mutations that result in constitutively open Kv11.1 channels, and the potential uses for cells having constitutively open Kv11.1 channels in the development of improved drug screening assays.

The human ether-a-go-go related gene (hERG) encodes the Kv11.1 protein α-subunits that underlie the rapidly activating delayed rectifier K+ current ($I_{Kr}$) in the heart. The α-subunits combine to form the Kv11.1 potassium channels, which function in cardiac myocytes as voltage-gated channels to restore resting membrane potential after action potential generation.

Drug-induced acquired long QT syndrome (LQTS) has become an important liability for clinically available drugs and developmental compounds. LQTS is a heart condition associated with prolongation of repolarization following depolarization of the cardiac ventricles. It is associated with fainting and sudden death due to ventricular arrhythmias.

The mechanism commonly proposed for drug-induced QT interval prolongation is direct block of Kv11.1 channels or its native current, $I_{Kr}$. The drugs bind to a structurally unique receptor domain in the pore-S6 region of the channel to suppress K+ ion permeation. Drug binding (block) usually occurs preferentially to the "open state" (ion conducting state) of the channels. Screening for unanticipated Kv11.1 channel block is now expected of all new drugs submitted for review to the FDA and to other regulatory agencies worldwide, and Kv11.1 channel block screening is commonly now done within the pharmaceutical industry early in the life-cycle of new compound development. In recent years, Kv11.1 channel block by drugs has become one of the most common reasons for drug withdrawal from the marketplace and for the termination of lead compounds in development.

Under normal conditions, Kv11.1 channels are in a closed or rested state, where drugs bind to the ion channel with low affinity. During cell depolarization the Kv11.1 channels become active (open) to conduct K+ ions, and drugs can access and bind to a drug binding domain located in the channel pore-S6 region of the Kv11.1 protein. Drugs bind with high affinity to this open state, thus this open state is key in studying drug binding (block) efficacy to the channel. Kv11.1 channels also can inactivate (cease conducting ions) and when cells repolarize the Kv11.1 channel again reopens before returning to the rested or closed state.

In the Kv11.1 channel protein the S4 transmembrane spanning segment, as with most ion channel proteins, contains multiple charged amino acids and is thought to be the voltage-sensor that responds to changes in the transmembrane voltage resulting in the channel pore opening to conduct K+ ions. The S1-S3 transmembrane spanning segments are less well studied, but also contain charged amino acid residues and these segments are thought to modify channel gating properties.

We have described below mutations in the transmembrane spanning segments of the Kv11.1 channel protein that unexpectedly cause the channel to remain open at all times. The example below shows that these constitutively open mutant Kv11.1 channels are blocked by channel-blocking drugs. Thus, the mutant Kv11.1 channels of the present invention could provide a more efficient and effective assay for studying the tendency of drugs and other compounds to bind and block the Kv11.1 channels and for assessing the risk for drug-induced LQTS.

BRIEF SUMMARY OF THE INVENTION

The present invention is both a cell and cell population having constitutively open Kv11.1 channels and a method for using this cell or cell population to screen compounds for Kv11.1 channel block activity.

In one embodiment, the present invention is a cell or cell population having two charge reversal mutations in the hERG gene coding for the Kv11.1 channel proteins. Specifically, the mutations cause amino acid substitutions at residues 466 and 534 of the wild type Kv11.1 amino acid sequence disclosed in SEQ ID NO: 1 that reverse the charges of those residues. These charge reversal mutations cause the Kv11.1 channel to be constitutively open at all physiologically relevant membrane potentials.

The pair of charge reversal mutations is selected from the group consisting of D466K/R534D, D466K/R534E, D466R/R534D, D466R/R534E, D466H/R534D, and D466H/R534E, with each combination resulting in the same reversal of charge. Preferably, the charge reversal pairs are D466K/R534D or D466K/R534E. The cell or cell population can be made of any cell type. Preferably, the cells are mammalian cells such as HEK293 cells, COS7 cells, or CHO cells.

In another embodiment, the present invention is a method of screening a test compound for Kv11.1 channel block activity. The method comprises exposing a cell or cell population having constitutively open Kv11.1 channels as described above to the compound to be tested, measuring the Kv11.1 channel block activity of the exposed cell or cell population, and comparing the channel block activity of the exposed cell or cell population to the channel block activity of an unexposed cell or cell population having constitutively open Kv11.1 channels. The Kv11.1 channel block activity can be measured using known techniques such as patch clamping, rubidium flux assays, labeled drug competition assays, or radioligand displacement binding.

Additional embodiments and features of the present invention are apparent to one skilled in the art upon review of the specification, claims, and drawings.

BRIEF SUMMARY OF THE SEVERAL VIEWS OF THE DRAWINGS

FIG. 3A shows Kv11.1 whole-cell patch clamp current measurements in wild type cells as the cells are exposed to increasing concentrations of the Kv11.1 channel-blocking drug Verapamil. For each concentration, cells were pre-pulsed from −80 to 20 mV, and the peak tail $I_{Kv11.1}$ (indicated by arrow on each graph) was measured at a test-pulse of −50 mV. Note the total experiment time of about 15 minutes. FIG. 3B shows whole-cell patch clamp current measurements in D466K/R534D double charge mutant cells at a constant cell potential of −50 mV as the cells are exposed to increasing concentrations of Verapamil. Note that the total time of this experiment is about one and a half minutes.

DETAILED DESCRIPTION OF THE INVENTION

The KCNH2 or human-Ether-a-go-go Related Gene (hERG) encodes Kv11.1 α-subunits that combine to form Kv11.1 potassium channels. The hERG gene is translated as a core-glycosylated immature 135 kDa protein (Kv11.1) in the endoplasmic reticulum and is converted to a complexly-glycosylated mature 155 kDa protein in the Golgi apparatus. Warmke J. W., et al. (A family of potassium channel genes related to eag in Drosophila and mammals. PNAS. 1994. 91(8):3438-3442 incorporated by reference) discloses the sequence and structure of the hERG gene and its wild type translation product, Kv11.1. The amino acid sequence for wild type Kv11.1 as disclosed in Warmke is identical to SEQ ID NO: 1 of this application, and all amino acid residue numbers in this application refer to SEQ ID NO: 1.

Figure 1:
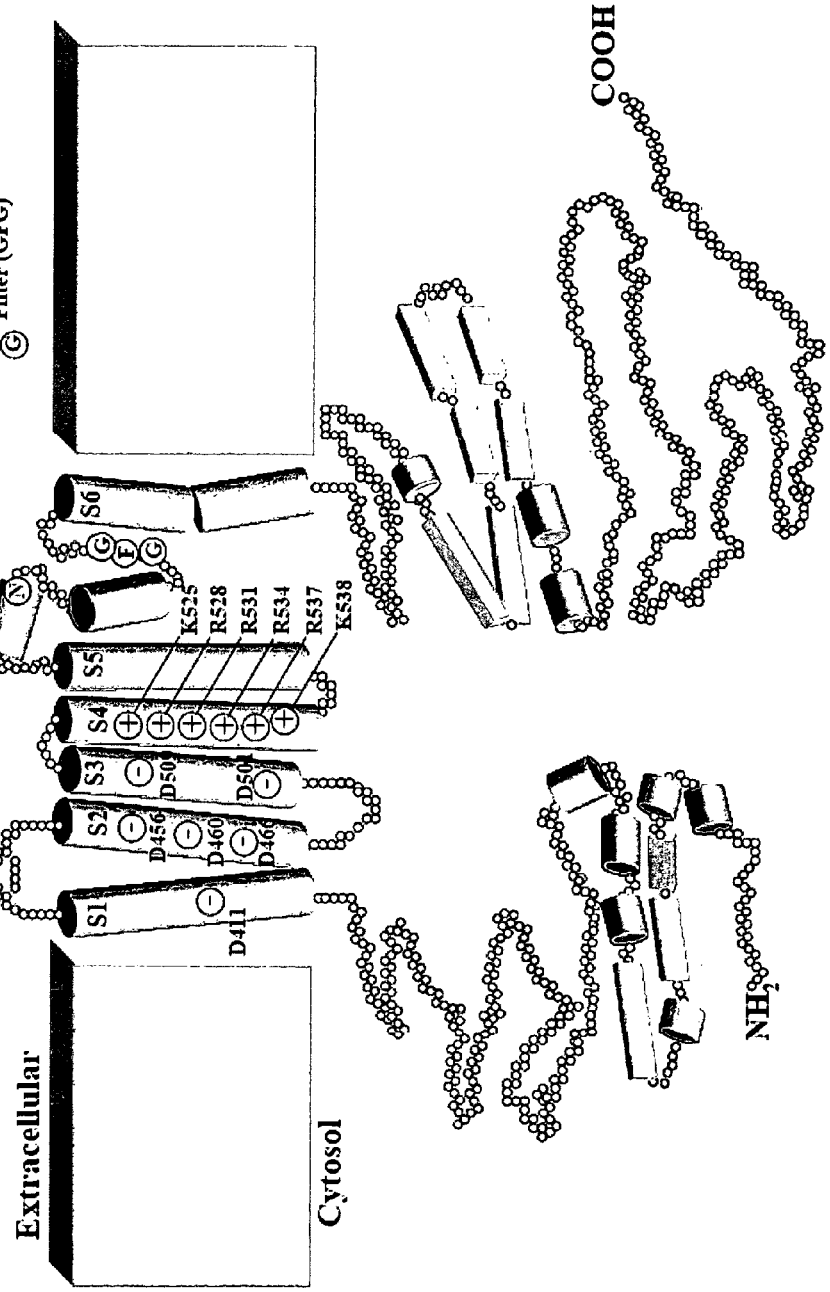
FIG. 1 is a sectional view of a wild type Kv11.1 protein α-subunit (labeled hERG1 in the drawing) embedded in the cell membrane. Amino acid residue numbers and identities correspond to the wild type Kv11.1 amino acid sequence of SEQ ID NO: 1. S6 and just before it is the channel pore region. In the present invention, amino acid residue 466 in region S2, which is shown in the wild type protein in the figure as a negative acidic residue (aspartate, D), is mutated to a positive basic amino acid residue. Conversely, amino acid residue 534 in region S4, which is shown in the wild type protein in the figure as a positive basic residue (arginine, R), is mutated to a negative acidic amino acid residue.

FIG. 1 is a sectional view of a wild type Kv11.1 protein subunit (labeled hERG1 in the drawing) embedded in the cell membrane. Amino acid residue numbers and identities shown in FIG. 1 correspond to the wild type Kv11.1 amino acid sequence of SEQ ID NO: 1. S6 is the channel pore region, and S1-S4 are the voltage sensor regions.

Several Kv11.1 mutations interfere with channel biogenesis and do not form the mature protein (trafficking-deficient). Introducing a second mutation can sometimes correct the trafficking-deficient phenotype (intragenic suppression; see Delisle, B. P., et al, Mol Pharmacol, 2005; 68:233-240).

We tested whether a trafficking-deficient mutation in the voltage-sensor regions of Kv11.1 can undergo intragenic suppression. These regions are shown as S1-S4 in FIG. 1. We created a number of charge reversal mutations, including D466K (wherein lysine is substituted for aspartate at amino acid residue 466 in the wild type Kv11.1 of SEQ ID NO:1), R534D (wherein aspartate is substituted for arginine at amino acid residue 534 in the wild type Kv11.1 of SEQ ID NO:1), and R534E (wherein glutamate is substituted for arginine at amino acid residue 534 in the wild type Kv11.1 of SEQ ID NO: 1). In addition, we created a number of double charge reversal mutations, including D466K/R534D and D466K/R534E. We created these mutations from WT-Kv11.1 cDNA and expressed these constructs in HEK293 cells (see Zhou, Z. et al., Biophys J, 1998b; 74:230-241).

Figure 2:
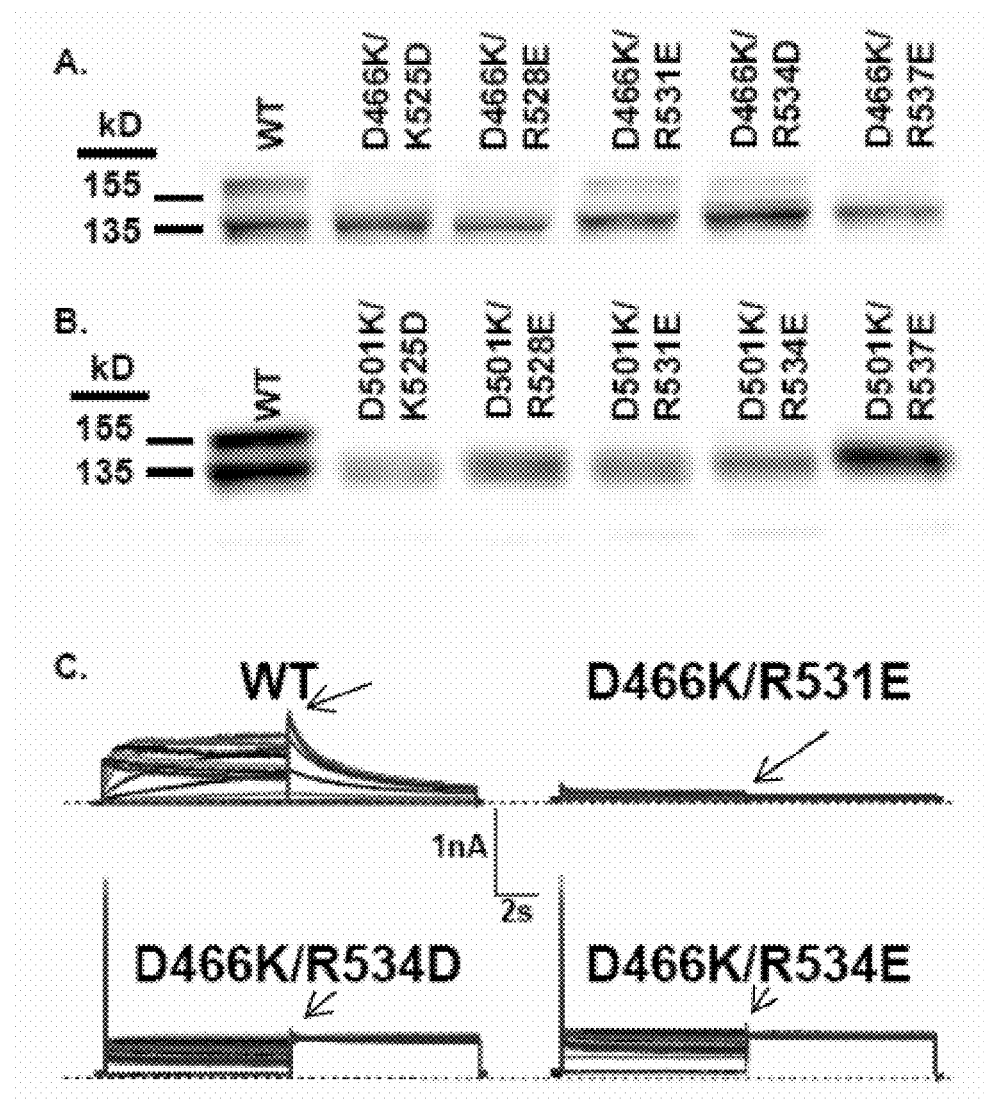
FIGS. 2A and B: Kv11.1 double charge reversal mutations D466K/R531E and D466K/R534D traffic to the membrane as mature proteins. The figure shows Western blot of wild type Kv11.1 and various double charge reversal mutations of Kv11.1. The immature protein is at the 135 kD band, and the mature protein is at the 155 kD band. In addition to wild type (WT), the D466K/R531E and D466K/R534D double charge reversal mutations show mature protein at the 155 kD band.
FIG. 2C: Double charge mutants D466K/R534D and D466K/R534E continuously conduct current, indicating that their Kv11.1 channels are constitutively open. Kv11.1 current ($I_{Kv11.1}$) was measured using the whole-cell patch clamp technique. Using a holding potential of −80 mV, cells were pre-pulsed from −80 to 40 mV in 10 mV increments and the peak tail $I_{Kv11.1}$ (indicated by arrow on each graph) was measured at a test-pulse of −50 mV. Cells expressing wild type (WT) channels pass no current at voltages negative to −50 mV because channels are closed, whereas depolarizing them above this causes increasing and decreasing current, corresponding to voltage-dependent opening, inactivation and closing of the Kv11.1 channels. The D466K/R531E double charge reversal mutant showed no current, indicating that the channels do not open. D466K/R534D and D466K/R534E double charge mutants both show a continuous current, indicating that the channels in those mutants are constitutively open. They do not close and only weakly inactivate.

Western blot analysis showed that the D466K mutants formed only the immature protein, whereas the R534D, D466K/R534D, and D466K/R534E mutants formed both immature and mature protein. FIGS. 2A and 2B illustrate this result for the D466K/R534D mutant. The figures show Western blot results for a number of the double charge reversal mutants. Of all the double mutant Western blots shown in FIGS. 2A and 2B, only D466K/R534D and D466K/R531E show production of mature protein (band at 155 kD). Western blots for R534D and D466K/R534E showed a similar pattern (data not shown).

We report that modifying two charged residues in regions S2 and S4 to reverse the charge of the residues dramatically modifies the behavior of Kv11.1 channels to cause them to be constitutively open at resting conditions and to traffic to the cell membrane. The specific double charge mutations we examined are D466K/R534D and D466K/R534E. As seen in FIG. 1, amino acid residue 466 is in the S2 region of the Kv11.1 protein, and amino acid residue 534 is in the S4 region. As the figure indicates, these two amino acid residues are in close proximity. These dual mutations "reverse" two charges, in principle allowing the amino acid pairs to still interact. These mutations substitute basic for acidic (R to D, R to E) residues or acidic for basic (D to K) residues in specific amino acid positions where amino acids are thought to interact. Whole-cell patch clamp studies show that these two double charge mutants are constitutively open (see FIG. 2C). Therefore, there is no need to activate (depolarize) the channel to cause it to enter the high affinity drug binding state.

Kv11.1 current ($I_{Kv11.1}$) was measured using the whole-cell patch clamp technique (See Delisle, B. P., et al, Mol Pharmacol, 2005; 68:233-240). Using a holding potential of −80 mV, cells were pre-pulsed from −80 to 40 mV in 10 mV increments and the peak tail $I_{Kv11.1}$ was measured at a test-pulse of −50 mV. The peak tail $I_{Kv11.1}$ measured during the test-pulse was plotted as a function of the pre-pulse potential and fit using a Boltzmann equation to calculate the midpoint potential for activation (V½) and the slope factor for maximal activation.

Cells expressing D466K had almost no $I_{Kv11.1}$. Compared to WT, R534D shifted the V½ positively (−17.9±1.7 vs. 0.0±1.0 mV, p<0.05) and increased the slope factor for maximal activation (7.0±1.0 vs. 4.8±1.0 mV/e-fold change, p<0.05) (data not shown). Cells expressing D466K/R534D and D466K/R534E double charge mutations were fully activated at −80 mV. This is illustrated in FIG. 2C, which shows a constant current in the patch clamp data for those two double charge mutants.

We conclude that D466K interferes with proper Kv11.1 biogenesis, that R534D alters activation and intragenically suppresses D466K, and that D466K/R534D and D466K/R534E were constitutively open at all physiologically relevant membrane potentials, ≧−80 mV in our example. A constantly open potassium channel will set the resting potential to whatever the membrane potassium gradient is.

Furthermore, we have demonstrated that the D466K/R534D channel retains the expected sensitivity to block by selective Kv11.1 and $I_{Kr}$ blocking drugs such as E-4031 and Verapamil, thus the drug binding domain of the Kv11.1 channel is intact. In addition, cells expressing the D466K/R534D double charge reversal mutation show much quicker and more precise reaction to channel-blocking drugs than cells expressing wild type Kv11.1, showing the potential to use the present invention for much faster and more efficient Kv11.1 channel blocking assays.

We performed Kv11.1 whole-cell patch clamp current measurements in wild type cells as the cells were exposed to increasing concentrations of the Kv11.1 channel-blocking drug Verapamil. The results of these experiments are shown in FIG. 3A. For each concentration, cells were pre-pulsed from −80 to 20 mV, and the peak tail $I_{Kv11.1}$ (indicated by arrow on each graph) was measured at a test-pulse of −50 mV. Note the total experiment time of about 15 minutes.

We also performed whole-cell patch clamp current measurements in D466K/R534D double charge mutant cells at a constant cell potential of −50 mV as the cells were exposed to increasing concentrations of Verapamil. The results of this experiment are shown in FIG. 3B. Note that FIG. 3B shows distinct and stabilized current measurements at 0.1, 1, and 10 µM concentrations of Verapamil. In addition, the total time for the experiment was about one and a half minutes, about ten times faster than the similar series of experiments in wild type cells shown in FIG. 1A. The results shown in the figure illustrate the dramatic potential for the use of the double charge mutant cells to test for Kv11.1 block much more quickly and efficiently.

Figure 4:
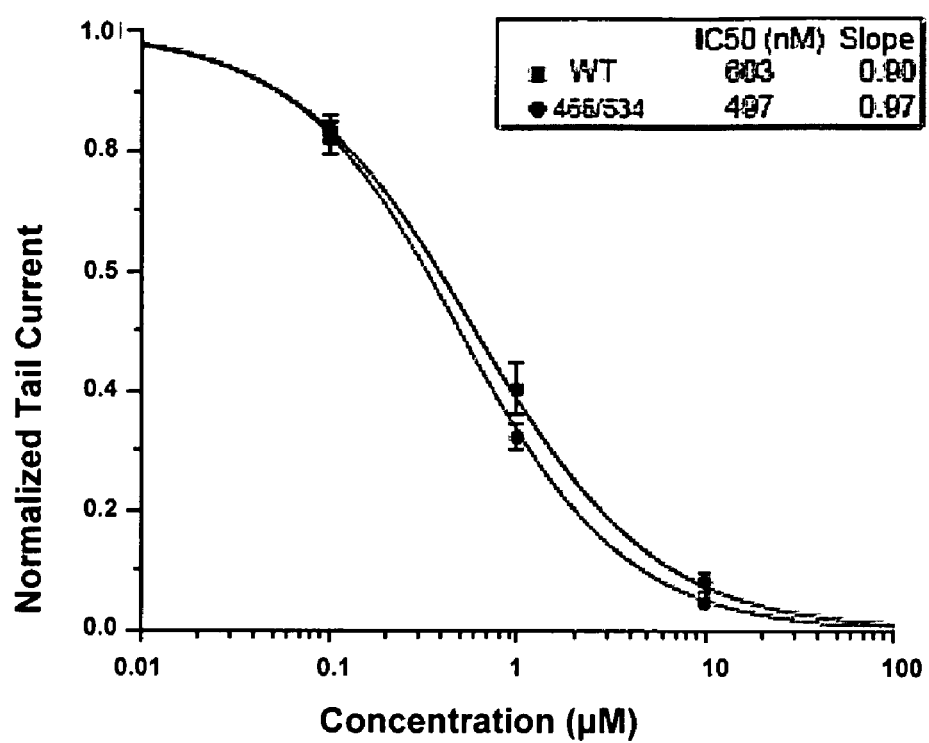
FIG. 4: Wild type and D466K/R534D double charge mutants show similar drug-block sensitivities in whole-cell patch clamp experiments. Normalized peak tail current is shown as a function of the concentration of Verapamil used for both wild type and D466K/R534D double charge mutants. The concentration-response relations are nearly identical, and the IC50 values (50% drug block) are not statistically different.

Wild type and D466K/R534D double charge mutants show similar drug-block sensitivities in whole-cell patch clamp experiments. We calculated normalized peak tail current and plotted it as a function of concentration Verapamil for both wild type and D466K/R534D double charge mutants. The results of these experiments are illustrated in FIG. 4. The double charge reversal mutant shows similar sensitivity (IC50 concentration and slope) to Kv11.1 channel drug block as wild type cells.

Individual mutations, such as D466K, R534D and R534E do not display the constitutively open channel behavior of the present invention. Other double charge reversal amino acid substitutions at residues 466 and 534 of SEQ ID NO: 1 will produce similar constitutively open channel behavior. For example, we have expressed the D466R/R534D double mutation (D466R being a charge reversal mutation wherein arginine is substituted for aspartate at amino acid residue 466 in the wild type Kv11.1 of SEQ ID NO: 1) in HEK293 cells, and have produced limited data showing that these cells have properties similar to properties of other constitutively open channel mutants. Other combinations, such as using the D466H charge reversal mutation at residue 466 (wherein histidine is substituted for aspartate at amino acid residue 466 in the wild type Kv11.1 of SEQ ID NO:1) may also be used to create a double charge reversal mutation resulting in constitutively open Kv11.1 channels.

Thus, in one embodiment, the present invention is a cell comprising a double mutation in the hERG gene wherein the mutation causes a charge reversal mutation of both the amino acid residues 466 and 534 of the wild type Kv11.1 protein sequence of SEQ ID NO: 1. Preferably, the mutant is D466K/R534D or D466K/R534E. However, other charge reversal mutants, including D466R/R534D, D466R/R534E, D466H/R534D, and D466H/R534E would be suitable.

In addition, other mutations could be combined with the double charge reversal mutation of the present invention. For example, we have created a D466K/R534E/S620T mutant (additionally comprising the mutation wherein threonine is substituted for serine at amino acid residue 620 in the wild type Kv11.1 of SEQ ID NO: 1) in which the Kv11.1 channels remain open at very high voltage.

These mutations may be made from a wild type Kv11.1 cDNA using techniques known in the art. We have expressed these constructs in HEK293 cells, but anticipate that one may wish to use other mammalian cell types, such as COS7 cells or CHO cells. Other cells, both mammalian and non-mammalian, would be suitable to express the mutation and would result in the same advantageous phenotype of constitutively open Kv11.1 channels at a cell's resting potential. For example, one may wish to use mammalian cells such as native heart cells or human embryonic stem cell-derived cell types, including cardiomyocytes. Or one may wish to use non-mammalian cells such as *Xenopus oocyte*.

A Kv11.1 channel having constitutively open properties is useful because screening for unanticipated Kv11.1 channel block is now expected of all new drugs submitted for review to the FDA and to other regulatory agencies worldwide, and Kv11.1 screening is commonly now done within the pharmaceutical industry early in the life-cycle of new compound development. The screening tests utilize technologies of measuring channel current such as patch clamping, rubidium flux assays, labeled drug competition assays (dofetilide displacement assay) and rescue (restoring protein trafficking) of mutant (G601S-Kv11.1) channels. All but the last assay require that the channel be in the open state (the highest drug binding affinity) to optimally assess drug binding, whereas the last assay requires very high drug concentrations to have an effect. When compared to conventional patch clamp method for assessing Kv11.1 channel block, these other methods lack quantitative accuracy.

Patch clamping measures the movement of charge as electric current (here potassium ions moving through potassium selective membrane channels). A reduction in current amplitude in cells exposed to a test compound as compared to current amplitude measured in unexposed control cells equates to block of the channel by the test compound.

Rubidium flux assays measure rubidium movement (potassium channels are also permeable to rubidium) through open channels using either radioactive rubidium (86Rb) or cold rubidium measured by an atomic absorption spectrometer, which can detect tiny amounts of rubidium accurately. Cells must first be loaded with rubidium (soaked in it for a few hours). A decrease in flux into the bath from the cells exposed to a test compound as compared to the flux of unexposed control cells equates to block of the channel by the test compound. Similar flux assays use potassium-42 (42K) radiotracers in pharmacological and toxicological studies of potassium channels.

Labeled drug competition, also known as radioligand displacement assays, utilize test compound displacement of a previously high-affinity bound radiolabled compound (radiolabled dofetilide, astemizole, etc). An increase in the amount of radiolabled compound in the cell bath of cells exposed to a test compound as compared to the amount of radiolabled compound in the cell bath of unexposed control cells equates to binding (therefore block) to the channel by the test compound.

The following is an example of a patch clamping protocol that is presently used to investigate a new compound's Kv11.1 channel block activity: Cells expressing WT Kv11.1 channels are pipetted into the study chamber maintained at physiological temperature. The whole cell patch clamp recording configuration is achieved and series resistance and cell capacitance compensation are applied. A voltage step protocol, such as that shown in FIG. 3A, is applied to measure $I_{Kv11.1}$ in the absence and presence of test compound, positive control, or negative control, as follows. From a holding potential of −80 mV, a voltage step to 20 mV is applied for 5 sec to maximally activate Kv11.1 channels followed by the test step to −50 mV for 4 sec to elicit the Kv11.1 tail current, before returning to the holding potential. The voltage step protocol is repeated at 15 sec intervals.

During patch clamp recordings, cells are first superfused constantly with extracellular saline until a steady level of $I_{Kv11.1}$ is achieved. Then, a low concentration of test compound (in extracellular saline) is applied until a steady level Of $I_{Kv11.1}$ is achieved. This process is repeated for progressively higher concentrations of test compound until a predetermined maximal concentration is reached. At each test compound concentration the steady-state peak tail current is measured for 4 cells and averaged together to give the mean value±standard deviation. These values are then plotted as in FIG. 4 to give a concentration-response relation and the IC50 value (if the test compound causes block). A positive control (drug known to block $I_{Kv11.1}$) and a negative control are also included. Superperfusion is computer controlled and linked to the voltage stimulus protocols. For some test compounds, particularly those that bind slowly to the channel, only a single concentration can be studied on a cell, requiring that a new cell be used for each test compound concentration.

Figure 3:
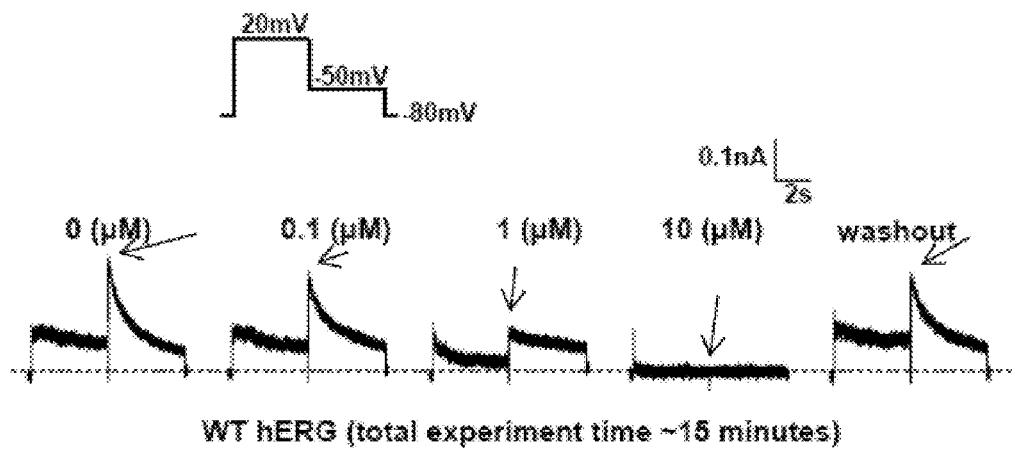
FIG. 3: Constitutively open channels are sensitive to drug-induced Kv11.1 channel block.
Figure 3:
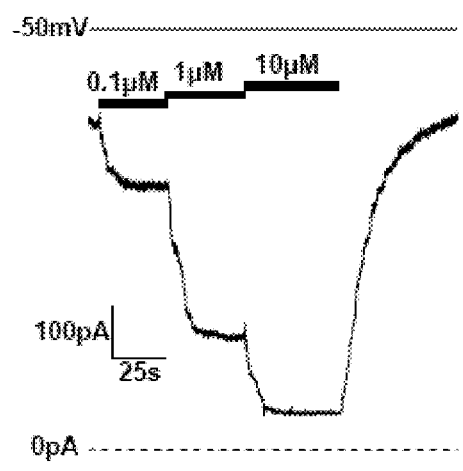

The charge reversal mutations of the present invention will permit the development of simpler, high-throughput, and possibly more accurate Kv11.1 binding assays because the Kv11.1 channel is always in the activated or open state to which drugs bind. For example, the data presented in FIG. 3 illustrate the potential for using cells with constitutively open Kv11.1 channels in modified patch clamp measurement protocols that are much faster than the standard protocol outlined above.

Whether one is dealing with patch clamping, flux assays or drug displacement assays, a central requirement is that the Kv11.1 channel must be depolarized to open the channel. Patch clamping does this directly through applying an electrical potential, and flux and displacement assays do this by increasing potassium in the bath to depolarize the cells. In flux and displacement assays, potassium depolarization will open only a fraction of WT Kv11.1 channels, and these assays presently do not produce the same IC50 values as patch clamping, making them less useful in quantitative measurements of channel block activity.

However, because the constitutively open Kv11.1 channels of the present invention are always in the high-affinity open drug binding state, there is no need to depolarize the cells. This problematic and time-consuming step can be eliminated. Thus in addition to making the all assay types much faster, the constitutively open Kv11.1 channels have the potential to make flux and displacement assays comparable in accuracy to patch clamp studies. The above are just a few examples of how these unique charge reversal mutations could significantly impact drug screening.

A second potential application of the present invention is that the charge reversal mutations, preferably, D466K/R534D and D466K/R534E mutations, could allow for the successful expression of certain ion channels (e.g., calcium channels) in stable cell lines, where the negative resting potential (−80 mV) of an open Kv11.1 channel could maintain the cell voltage below that voltage where calcium channels open. By causing calcium channels to remain closed, this would prevent cells from loading with potentially lethal amounts of calcium.

We claim:

1. A cell comprising at least one constitutively open Kv11.1 channel wherein the Kv11.1 channel comprises at least two mutations, wherein amino acid residues of opposite charge substitute for residues 466 and 534 of the wild type Kv11.1 amino acid sequence disclosed in SEQ ID NO:1.

2. The cell of claim 1 wherein the pair of charge reversal mutations is selected from the group consisting of D466K/R534D and D466K/R534E.

3. The cell of claim 1 wherein the pair of charge reversal mutations is selected from the group consisting of D466R/R534D, D466R/R534E, D466H/R534D, and D466H/R534E.

4. The cell of claim 1 wherein the cell is a mammalian cell.

5. The cell of claim 4 wherein the cell is a HEK293 cell.

6. The cell of claim 4 wherein the cell is selected from the group consisting of a COS7 cell, a CHO cell, a native heart cell, and a cardiomyocyte.

7. A cell population comprising more than one of the cells of claim 1.

* * * * *

SEQUENCE LISTING

```
<160> NUMBER OF SEQ ID NOS: 1

<210> SEQ ID NO 1
<211> LENGTH: 1159
<212> TYPE: PRT
<213> ORGANISM: Homo Sapiens

<400> SEQUENCE: 1

Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60
```

-continued

```
Thr Cys Asp Phe Leu His Gly Pro Arg Thr Gln Arg Ala Ala Ala
 65                  70                  75                  80

Gln Ile Ala Gln Ala Leu Leu Gly Ala Glu Arg Lys Val Glu Ile
             85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
            115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Ala Gly Gly Ala Gly Ala Pro Gly
            180                 185                 190

Ala Val Val Asp Val Asp Leu Thr Pro Ala Ala Pro Ser Ser Glu
            195                 200                 205

Ser Leu Ala Leu Asp Glu Val Thr Ala Met Asp Asn His Val Ala Gly
210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
            275                 280                 285

Glu Ala Met Arg Ala Gly Val Leu Pro Pro Pro Arg His Ala Ser
            290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350

Thr Ser Asp Arg Glu Ile Ile Ala Pro Lys Ile Lys Glu Arg Thr His
            355                 360                 365

Asn Val Thr Glu Lys Val Thr Gln Val Leu Ser Leu Gly Ala Asp Val
370                 375                 380

Leu Pro Glu Tyr Lys Leu Gln Ala Pro Arg Ile His Arg Trp Thr Ile
385                 390                 395                 400

Leu His Tyr Ser Pro Phe Lys Ala Val Trp Asp Trp Leu Ile Leu Leu
                405                 410                 415

Leu Val Ile Tyr Thr Ala Val Phe Thr Pro Tyr Ser Ala Ala Phe Leu
            420                 425                 430

Leu Lys Glu Thr Glu Glu Gly Pro Pro Ala Thr Glu Cys Gly Tyr Ala
            435                 440                 445

Cys Gln Pro Leu Ala Val Asp Leu Ile Val Asp Ile Met Phe Ile
450                 455                 460

Val Asp Ile Leu Ile Asn Phe Arg Thr Thr Tyr Val Asn Ala Asn Glu
465                 470                 475                 480

Glu Val Val Ser His Pro Gly Arg Ile Ala Val His Tyr Phe Lys Gly
```

-continued

```
                485                 490                 495
Trp Phe Leu Ile Asp Met Val Ala Ile Pro Phe Asp Leu Leu Ile
                500                 505                 510

Phe Gly Ser Gly Ser Glu Glu Leu Ile Gly Leu Leu Lys Thr Ala Arg
                515                 520                 525

Leu Leu Arg Leu Val Arg Val Ala Arg Lys Leu Asp Arg Tyr Ser Glu
                530                 535                 540

Tyr Gly Ala Ala Val Leu Phe Leu Leu Met Cys Thr Phe Ala Leu Ile
545                             550                 555                 560

Ala His Trp Leu Ala Cys Ile Trp Tyr Ala Ile Gly Asn Met Glu Gln
                565                 570                 575

Pro His Met Asp Ser Arg Ile Gly Trp Leu His Asn Leu Gly Asp Gln
                580                 585                 590

Ile Gly Lys Pro Tyr Asn Ser Ser Gly Leu Gly Gly Pro Ser Ile Lys
                595                 600                 605

Asp Lys Tyr Val Thr Ala Leu Tyr Phe Thr Phe Ser Ser Leu Thr Ser
                610                 615                 620

Val Gly Phe Gly Asn Val Ser Pro Asn Thr Asn Ser Glu Lys Ile Phe
625                             630                 635                 640

Ser Ile Cys Val Met Leu Ile Gly Ser Leu Met Tyr Ala Ser Ile Phe
                                645                 650                 655

Gly Asn Val Ser Ala Ile Ile Gln Arg Leu Tyr Ser Gly Thr Ala Arg
                660                 665                 670

Tyr His Thr Gln Met Leu Arg Val Arg Glu Phe Ile Arg Phe His Gln
                675                 680                 685

Ile Pro Asn Pro Leu Arg Gln Arg Leu Glu Glu Tyr Phe Gln His Ala
                690                 695                 700

Trp Ser Tyr Thr Asn Gly Ile Asp Met Asn Ala Val Leu Lys Gly Phe
705                             710                 715                 720

Pro Glu Cys Leu Gln Ala Asp Ile Cys Leu His Leu Asn Arg Ser Leu
                                725                 730                 735

Leu Gln His Cys Lys Pro Phe Arg Gly Ala Thr Lys Gly Cys Leu Arg
                740                 745                 750

Ala Leu Ala Met Lys Phe Lys Thr Thr His Ala Pro Pro Gly Asp Thr
                755                 760                 765

Leu Val His Ala Gly Asp Leu Leu Thr Ala Leu Tyr Phe Ile Ser Arg
                770                 775                 780

Gly Ser Ile Glu Ile Leu Arg Gly Asp Val Val Val Ala Ile Leu Gly
785                             790                 795                 800

Lys Asn Asp Ile Phe Gly Glu Pro Leu Asn Leu Tyr Ala Arg Pro Gly
                                805                 810                 815

Lys Ser Asn Gly Asp Val Arg Ala Leu Thr Tyr Cys Asp Leu His Lys
                820                 825                 830

Ile His Arg Asp Asp Leu Leu Glu Val Leu Asp Met Tyr Pro Glu Phe
                835                 840                 845

Ser Asp His Phe Trp Ser Ser Leu Glu Ile Thr Phe Asn Leu Arg Asp
                850                 855                 860

Thr Asn Met Ile Pro Gly Ser Pro Gly Ser Thr Glu Leu Glu Gly Gly
865                             870                 875                 880

Phe Ser Arg Gln Arg Lys Arg Lys Leu Ser Phe Arg Arg Arg Thr Asp
                                885                 890                 895

Lys Asp Thr Glu Gln Pro Gly Glu Val Ser Ala Leu Gly Pro Gly Arg
                900                 905                 910
```

```
Ala Gly Ala Gly Pro Ser Ser Arg Gly Arg Pro Gly Pro Trp Gly
        915                 920                 925

Glu Ser Pro Ser Ser Gly Pro Ser Ser Pro Glu Ser Ser Glu Asp Glu
    930                 935                 940

Gly Pro Gly Arg Ser Ser Ser Pro Leu Arg Leu Val Pro Phe Ser Ser
945                 950                 955                 960

Pro Arg Pro Pro Gly Glu Pro Pro Gly Gly Glu Pro Leu Met Glu Asp
                965                 970                 975

Cys Glu Lys Ser Ser Asp Thr Cys Asn Pro Leu Ser Gly Ala Phe Ser
            980                 985                 990

Gly Val Ser Asn Ile Phe Ser Phe Trp Gly Asp Ser Arg Gly Arg Gln
            995                 1000                1005

Tyr Gln Glu Leu Pro Arg Cys Pro Ala Pro Thr Pro Ser Leu Leu
    1010            1015                1020

Asn Ile Pro Leu Ser Ser Pro Gly Arg Arg Pro Arg Gly Asp Val
    1025            1030                1035

Glu Ser Arg Leu Asp Ala Leu Gln Arg Gln Leu Asn Arg Leu Glu
    1040            1045                1050

Thr Arg Leu Ser Ala Asp Met Ala Thr Val Leu Gln Leu Leu Gln
    1055            1060                1065

Arg Gln Met Thr Leu Val Pro Pro Ala Tyr Ser Ala Val Thr Thr
    1070            1075                1080

Pro Gly Pro Gly Pro Thr Ser Thr Ser Pro Leu Leu Pro Val Ser
    1085            1090                1095

Pro Leu Pro Thr Leu Thr Leu Asp Ser Leu Ser Gln Val Ser Gln
    1100            1105                1110

Phe Met Ala Cys Glu Glu Leu Pro Pro Gly Ala Pro Glu Leu Pro
    1115            1120                1125

Gln Glu Gly Pro Thr Arg Arg Leu Ser Leu Pro Gly Gln Leu Gly
    1130            1135                1140

Ala Leu Thr Ser Gln Pro Leu His Arg His Gly Ser Asp Pro Gly
    1145            1150                1155

Ser
```